(12) United States Patent
Gotschlich et al.

(10) Patent No.: US 6,664,094 B1
(45) Date of Patent: Dec. 16, 2003

(54) NEISSERIAL VACCINE FREE OF IMMUNOLOGICALLY FUNCTIONAL PIII OR CLASS 4 PROTEINS

(75) Inventors: Emil Claus Gotschlich, New York, NY (US); Lee Mark Wetzler, New York, NY (US); Milan Scott Blake, New York, NY (US); John Michael Koomey, Ann Arbor, MI (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 08/309,620

(22) Filed: Sep. 21, 1994

Related U.S. Application Data

(63) Continuation of application No. 08/150,235, filed on Nov. 9, 1993, now abandoned, which is a continuation of application No. 07/808,954, filed on Dec. 13, 1991, now abandoned, which is a continuation of application No. 07/212,786, filed on Jun. 29, 1988, now abandoned.

(51) Int. Cl.$^7$ .................. C12N 1/00; A61K 39/095
(52) U.S. Cl. .................. 435/243; 435/259; 435/822; 435/821; 436/543; 436/547; 424/249.1; 424/250.1; 424/234.1; 530/412
(58) Field of Search .................. 424/184.1, 197.11, 424/249.1, 250.1, 234.1, 242.1; 435/245, 822, 871, 243, 259; 530/412; 436/543, 547

(56) References Cited

U.S. PATENT DOCUMENTS

| | | | |
|---|---|---|---|
| 4,203,971 A | 5/1980 | Buchanan | 424/92 |
| 4,208,480 A | 6/1980 | D'Amato et al. | 435/34 |
| 4,220,638 A | 9/1980 | Karkhanis et al. | 424/92 |
| 4,239,749 A | 12/1980 | Buchanan | 424/92 |
| 4,241,045 A | 12/1980 | Gaafar | 424/1 |
| 4,330,623 A | 5/1982 | Karkhanis | 435/68 |
| 4,351,761 A | 9/1982 | Gaafar | 260/112 |
| 4,446,230 A | 5/1984 | Zubrzycki | 435/6 |
| 4,461,838 A | 7/1984 | Brinton et al. | 436/511 |
| 4,497,900 A | 2/1985 | Abram et al. | 436/511 |
| 4,584,195 A | 4/1986 | Schoolnik et al. | 424/92 |
| 4,622,223 A * | 11/1986 | Schoolnik et al. | 424/42 |
| 4,659,658 A | 4/1987 | McCarthy et al. | 435/34 |
| 4,681,761 A * | 7/1987 | Mietzner et al. | 424/92 |
| 4,696,896 A * | 9/1987 | Brinton et al. | 435/7 |
| 4,707,543 A | 11/1987 | Zollinger et al. | 424/92 |

FOREIGN PATENT DOCUMENTS

| | | | |
|---|---|---|---|
| EP | 0002645 | 6/1979 | A61K/39/02 |
| EP | 0089939 | 9/1983 | A61K/31/70 |
| EP | 0090660 | 10/1983 | A61K/39/095 |
| EP | 0182401 | 5/1986 | A61K/39/00 |
| WO | 84/04654 | 10/1985 | C07C/103/52 |

OTHER PUBLICATIONS

Jiskoot et al I&I 54! 333–338, 1986 Immunogenic Activity of Gonococcal Protein I in Mice with Three Different Lipoidal Adjuvants Delivered in Liposomes and in Complexes.*
Jiskoot et al Immunogenic Activity of Gonococcal Protein I in Mice with Three Different Lipoidal Adjuvants Delivered in Liposomes and in Complexes.*
Johnson et al The Journal of Infectious Dis 163:128–134 1991, Human Immunization with Pgh–3–2 Gonococcal Pilus Results in Cross–Reactive Antibody to the Cyanogen Bromide Fragment–2 of Pilin.*
Schoolnik et al Chapter 34 of NEW GENERATION VACCINE, pp. –565–597.*
Jiskool et al Infect & Imm 54:333–338, 1986.*
Wallace, R. et al., *Can. J. Microbiol.* 24: 124–128 (1978).
Apicella, M. et al., *Infect. Immun.* 26: 870–74 (1979).
McShan, W.M. et al., *Infect. Immun.* 55: (12): 3017–3022 (1987).
Koomey J.M. et al., *PNAS* 79 (12): 7881–7885 (1982).
Swanson, J. et al., *Infect. Immun.* 38: 668–672 (1982).
McDade, R.L., et al., *J. Bacteriol.* 141: 1183–1191 (1980).
Rice, P.A. et al., *J.Exp.Med.* 164: 1735–1748 (1986).
Arminson, P., Abst. Annual Meeting American Society for Microbiology, 118 (1987).

* cited by examiner

*Primary Examiner*—Patricia A. Duffy
(74) *Attorney, Agent, or Firm*—White & Case LLP

(57) ABSTRACT

This invention relates to mutants of Neisseria useful for vaccine preparation. Specifically this invention relates to mutants of Neisseria containing mutations in a major outer membrane protein gene such that no immunologically functional polypeptides encoded by said gene are produced. More specifically, the invention relates to a mutant strain of *Neisseria gonorrhoeae* having a mutation of the PIII gene and to vaccines derived therefrom.

24 Claims, 2 Drawing Sheets

US 6,664,094 B1

NEISSERIAL VACCINE FREE OF IMMUNOLOGICALLY FUNCTIONAL PIII OR CLASS 4 PROTEINS

Figure 1:
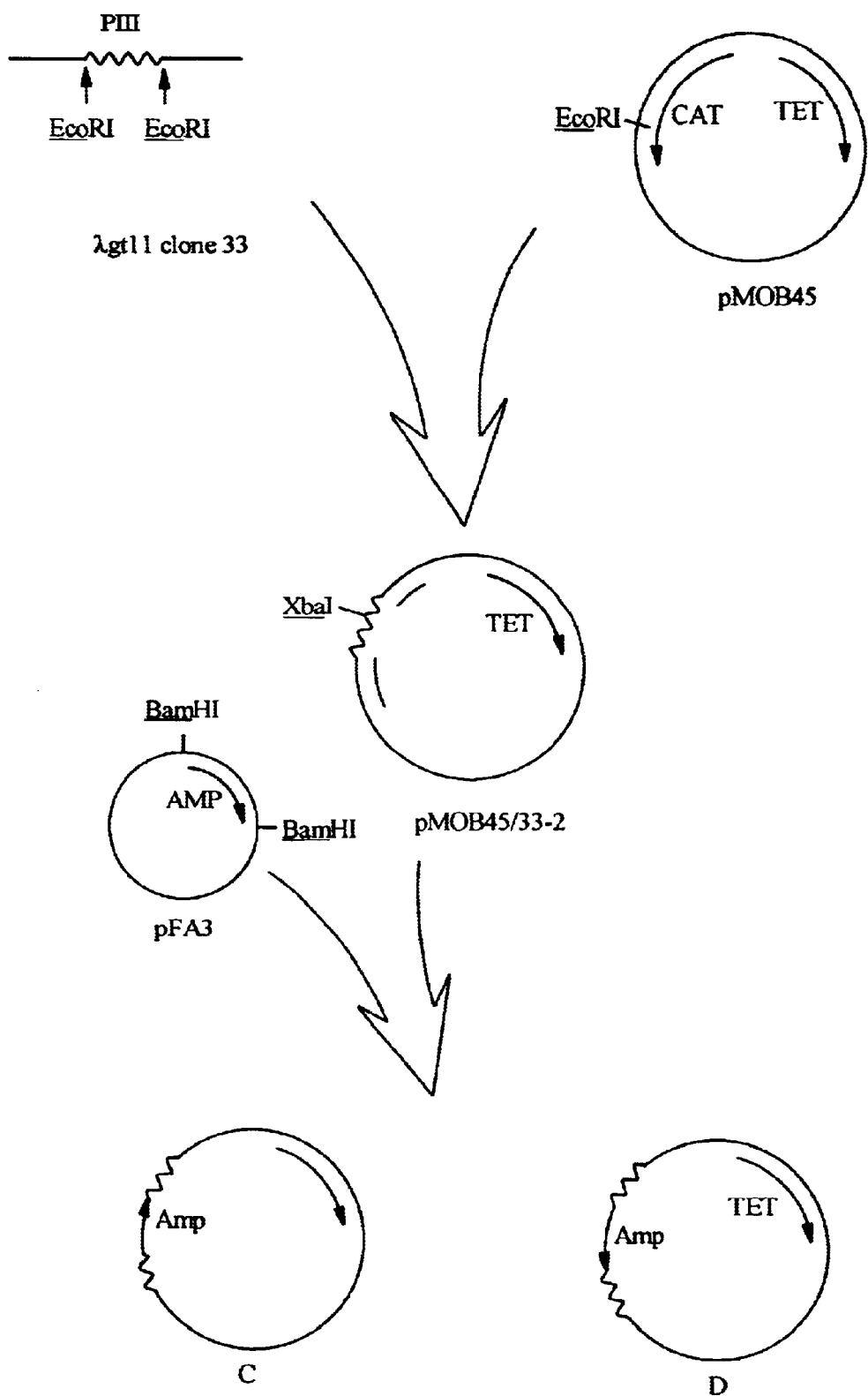
Figure 2:
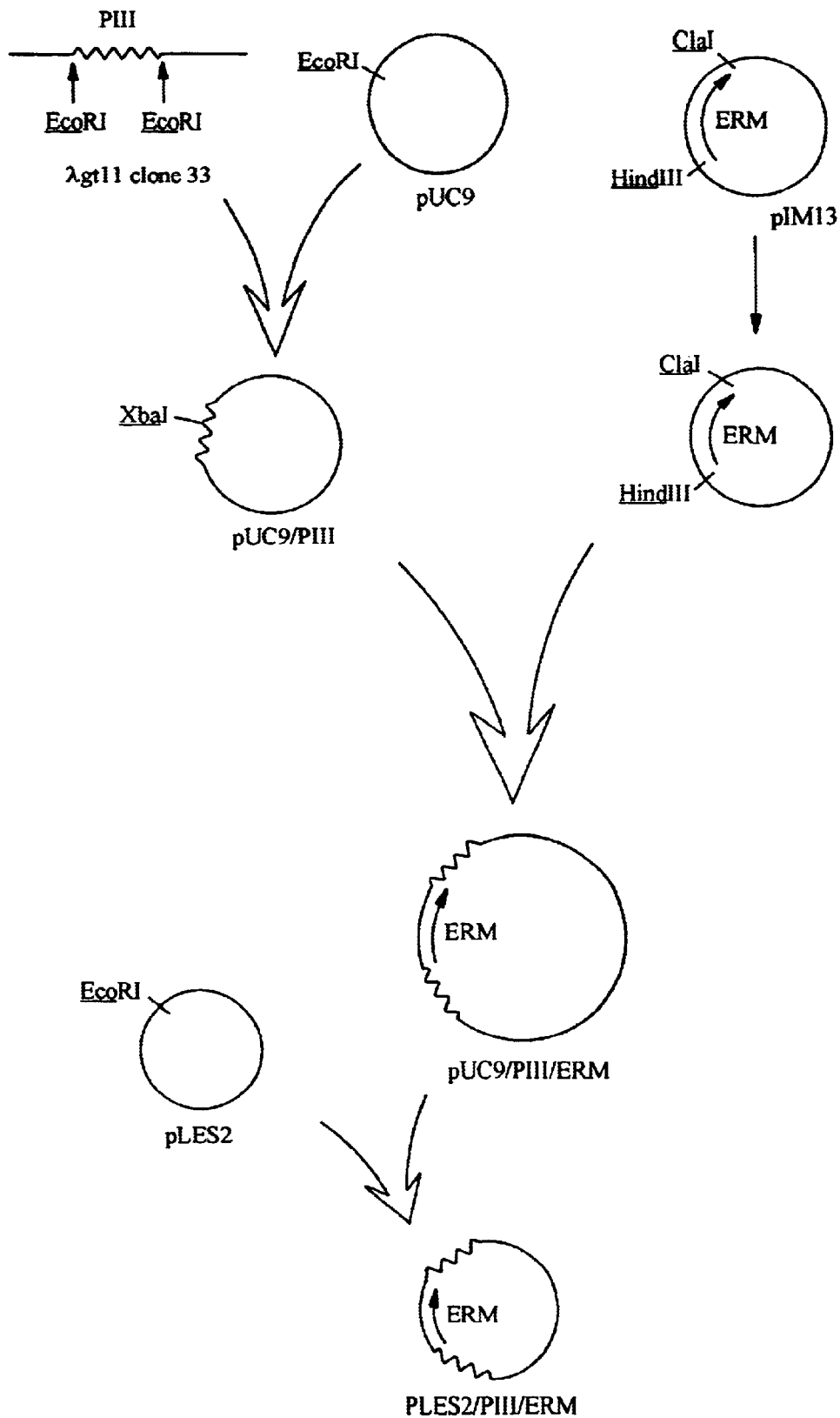

This application is a continuation application of U.S. Ser. No. 08/150,235, filed Nov. 9, 1993, now abandoned, which was a continuation application of U.S. Ser. No. 07/808,954, filed Dec. 13, 1991, now abandoned, which was a continuation application of U.S. Ser. No. 07/212,786, filed Jun. 29, 1988, now abandoned.

This invention was made with Government support under Grant No. A1-10615 from the National Institutes of Health. The Government may have certain rights in this invention.

FIELD OF THE INVENTION

This invention relates to mutants of Neisseria useful for vaccine preparation. Specifically this invention relates to mutants of Neisseria containing mutations in a major outer membrane protein gene such that no immunologically functional polypeptides encoded by said gene are produced. More specifically, the invention relates to a mutant strain of *Neisseria gonorrhoeae* having a mutation of the PIII gene and to vaccines derived therefrom.

BACKGROUND OF THE INVENTION

The genus Neisseria includes two species of gram-negative pyogenic cocci that are pathogenic to man: the meningococcus, *Neisseria meningitidis*, the causative agent of cerebrospinal meningitis, also referred to meningococcal meningitis and the gonococcus, *Neisseria gonorrhoeae*, the causative agent of the venereal disease gonorrhea.

*Neisseria gonorrhoeae* is an aerobic diplococcus that ferments glucose but not maltose, a characteristic useful in distinguishing the species from meningococci. Gonococci exhibit four colonial forms (T1–T4). Fresh isolates from clinical samples that retain their virulence grow as small colonies (T1 and T2). Repeated non-selective sub-culturing results in larger colonies (T3 and T4) which have been shown to be avirulent on inoculation in male volunteers.

Historically, the development of vaccines has been hampered by a number of technical problems inter alia, difficulty of cultivation, lack of a readily available and meaningful animal model, inability to classify the organisms by conventional serological techniques and the lack of protectiveness of whole bacterial cell vaccines when administered to humans.

Cell surface molecules are attractive candidates for vaccine compositions and have been extensively studied in bacteria in general and in Neisseria in particular.

Pilin-based Vaccines

Pili are proteinaceous, filamentous structures associated with the cell wall of infective strains of Neisseria. During infection the bacteria colonize the mucous membranes of the host; the attachment of the bacteria to the surface of the mucous membrane being mediated by the pili. Anti-pilin antibodies are thought to protect against infection by reacting with the pili and preventing the attachment of the bacterium to membrane target sites. Further the "coating action" of the antibody (i.e. opsonization) stimulates the removal of bacteria by phagocytic cells in the blood. U.S. Pat. Nos. 4,461,838 and 4,696,986 relate to crystalline and single rod structures derived from pili of Type 1 and Type 2 *Neisseria gonorrhoeae*, methods for their preparation and the use of such material in vaccines.

One of the major shortcomings of pilin-based vaccines is the high antigenic variability associated with the pilin protein, thus antibodies raised against one strain will not necessarily react with any other strain. U.S. Pat. Nos., 4,584,195 and 4,622,223 and PCT application No. PCT/US85/00565 attempt to address this problem by employing as vaccine components, fragments of the pilin proteins which comprise conserved amino acid sequences, thus antisera raised thereto are characterized by a somewhat broader reactivity.

Protein I (PI) Vaccines

Protein I is found in the membranes of all gonococci and is usually present in the largest amount. The protein has been purified and when inserted into artificial bilayers acts as an anion-selective pore. There appear to be 14–20 serotypic PI variants, however only one PI is expressed by any one strain. Further certain PI variants have been associated specifically with pelvic inflammatory desease (P.I.D.) and other variants with disseminated gonococcal infection (D.G.I.). For these reasons PI has been used as a vaccine component, U.S. Pat. Nos. 4,203,971 and 4,239,749 relate to methods of separating PI from outer membrane lipopolysaccharides which have been shown to have toxic properties and the use of the "detoxified" product as a vaccine. European Patent Application No. 83301813.8 points out some of the shortcomings of the above patents, such as low yields and low solubility, thus making the production of effective vaccines difficult. The European application discloses an improved purification protocol which results in a protein I preparation having a solubility of from 5 to 10 mg/ml. As described, the vaccine also contains small amounts of protein II and protein III as well as what is characterized as "trace" amounts of LPS (3.5–4.0%). As discussed in more detail below, these contaminants although present in only small amounts can have a significant adverse effect on the effectiveness of PI vaccines.

Protein II (PII) Vaccines

When observed with light directly reflected from the substage mirror of a colony microscope, gonococcal colonies vary in their opacity: some appear transparent like water droplets, others are opaque like ground glass, and other colonies are intermediate in appearance. Gonococci change from the transparent to the opaque phenotype (or vice versa) with great frequency, estimated to be $10^{-3}$ per cell division. The change to the opaque form is accompanied by the acquisition of one or more additional outer membrane proteins in the molecular weight range of 24,000–30,000. These proteins exhibit heat-modifiable behavior, namely, their apparent molecular weight on SDS-PAGE changes, depending on the degree to which they have been heated prior to electrophoresis. The optical property of opacity is due to the fact that the gonococci stick to each other within the colony and these zones of adhesion between outer membranes are mediated by the opaque proteins. This indicates that protein II binds to some constituent on the neighboring cell; however, this receptor-ligand relationship has not been defined. It has been noted that if all the colonial variants of a single strain are carefully examined as many as six different opaque proteins can be distinguished.

Although it is known that protein II is readily accessible to antibodies, very little information is available on the antibacterial effects that protein II antibodies might have. The limited serological data available currently indicate that these proteins are serologically specific, and the degree of cross-reactivity between them in the native state is not clearly delineated. The high degree of variability of this class of proteins has also discouraged interest in their use in a vaccine. Definitive estimates of the potential of protein II vaccines cannot be made until a much clearer picture emerges on their role (or quite likely multiple roles) in pathogenesis.

Protein III (PIII) Vaccines

It has been shown that all gonococcal strains examined have an outer membrane protein that is not heat modifiable and that in the absence of a reducing agent migrates on SDS-PAGE with a molecular weight of 30,000, but with a molecular weight of 31,000 following reduction. This protein, named protein III, does not seem subject to variation, with all strains having an identical protein as judged by peptide analysis. A hybridoma has been cloned that produces and antibody reactive with protein III as it exists in the membrane, indicating that at least one antigenic determinant is exposed to the surface (Swanson, J. et al., *Infect. Immunity* 38: 668–672 (1982)). In vivo cross-linking studies have shown that protein III is closely associated with the trimeric complex of protein (McDade R. L., et al., *J. Bacteriol.* 141: 1183–1191 (1980)).

The ubiquity and constancy of PIII initially made it an attractive candidate for vaccine, however, recent studies raise serious questions about the utility of PIII as a vaccine. For example, Rice, P. A. et al., (*J. Exp. Med.* 164: 1735–1748 (1986)) disclose that IgG antibodies directed against PIII act to block the killing of serum-resistant Neisseria by immune sera. As a result of eliciting these blocking antibodies, PIII quite paradoxically helps to protect the gonococcus from attack by antibodies to other surface antigens. Because it is technically very difficult to remove PIII from gonococcal membrane antigen preparations, vaccinations with PI results in, if anything, a diminished protective effect. (Arminson, P., Abst. Ann. Meeting American Society for Microbiology, 118 (1987)).

Other Antigen-based Vaccines

U.S. Pat. No. 4,220,638 and its cognate European Application No. 78400245.3 disclose the isolation and use of a macromolecular aggregate as a vaccine. The aggregate is characterized as being derived from the cell surface of Neisseria, having a molecular weight of $9.2 \times 10^6$ and having 5 major components which account for 80% by weight of the complex. One of the components has a molecular weight (~27,000) that is in the range of that reported for PIII (~30,000).

U.S. Pat. No. 4,330,623 relates to a method of solubilizing gonococcal antigens such as the macromolecular complex described above by treatment with trypsin.

The lipopolysaccharide (LPS) of the gonococcus (like that of the meningococcus) consists of only short oligosaccharies attached to a lipid A moiety. The sugars hat have been detected include KDO, glucose, galactose, heptose, glucosamine, and galactosamine. Studies on the antigenic properties of LPS indicate that there are determinants common to all gonococci that can be demonstrated using antiserum raised in hens (Wallace, R. et al., *Can. J. Microbiol.* 24: 124–128 (1978)) or monoclonal antibodies. However, there are also LPS serological determinants that allow classification of different gonococcal strains into six types (Apicella, M. et al., *Infect. Immun.* 26: 870–74 (1979)).

U.S. Pat. No. 4,681,761 relates to methods of purifying the major iron-regulated protein (MIRP) of *N. gonorrhoeae* and its use as a vaccine.

U.S. Pat. No. 4,351,761 discloses the purification an properties of the so-called "L-antigen" from *Neisseria gonorrhoeae* and its use in a diagnostic test to identify the presence of antibodies in human sera to *N. gonorrhoeae*.

U.S. Pat. No. 4,707,543 relates to a process for preparing a detoxified polysaccharide—outer membrane protein complex and its use as a vaccine.

European Patent Application No. 85201657.5 relates to a vaccine composition in which the antigenic activity of the protein is enhanced by the formulation of an absorbed antigen-detergent complex.

In an alternative approach, immunological reagents reactive with the pilus receptors on epithelial cells have been investigated as exemplified by European Patent Applications Nos. 83850077.5 and 86401916.1.

McShan, W. M. et al., (*Infection and Immunity* 55 (12): 3017–3022 (1987)) disclose the cloning and expression of genetic information derived from a serum resistant strain of gonococcus that confers serum resistance upon a serum sensitive strain. The DNA encodes a protein that can mediate the attachment of a blocking antibody to the cell surface. This blocking antibody interferes with the complement-mediated bactericidial antibody activity. Although similar in size, the protein, as the reference clearly shows, is antigenically unrelated to PIII.

Koomey, J. M. et al., (*Proc. Nat'l. Acad. Sci (USA).* 79(12): 7881–7885 (1982)), disclose the cloning and expression of a gonococcal gene (IgAl protease) in *E. coli*. The article also discloses deleting a portion of the cloned gene and inserting a marker gene therein. The resulting DNA is incapable of expressing the cloned gene product. This DNA is then used to transform normal gonococci to yield mutant strains in which the defective gene has been integrated into the bacterial chromosome by a double-crossover event.

Finally, a large number of patents exist which relate to the diagnosis of Neisseria. See, for example, U.S. Pat. Nos. 4,208,480, 4,241,045, 4,446,230, 4,497,900 and 4,659,658.

BRIEF DESCRIPTION OF INVENTION

The invention relates to novel mutants of *Neisseria gonorrhoeae* and the use of such strains in the preparation of an improved vaccine for the prevention of gonococcal infections. More specifically the invention relates to strains of *N. gonorrhoeae* in which the gene for Protein III (PIII) has been inactivated. PIII is a highly conserved, antigenically stable gonococcal outer membrane protein. Although PIII appears to be an ideal candidate as an active ingredient in a vaccine, it has been demonstrated that the antibodies elicited in response to PIII actually inhibit the bactericidal activity of immune serum against gonococci. These so-called blocking antibodies seriously limit the effectiveness of prior art vaccines derived from outer membrane components because an antigenically significant amount of PIII co-purifies with the desired antigen even in the case of relatively pure antigen preparations. The development of a strain incapable of producing immunologically functional PIII provides a useful source of other outer membrane antigens without the problem of PIII contamination.

The subject invention may be viewed as having several embodiments. The invention relates to a biologically pure culture of a mutant strain of the genus Neisseria incapable of producing a protein that elicits blocking antibodies or immunologically reacts with said antibodies. In a further embodiment the invention relates to a vaccine comprising an immunologically effective amount of an antigen derived from a strain of Neisseria incapable of producing immunologically functional PIII-like protein admixed with a physiologically acceptable excipient. In a yet another embodiment the invention relates to an antigen substantially free of PIII-like protein obtained from a strain of Neisseria incapable of producing PIII-like protein. In yet another embodiment the invention relates to an improvement in a method of preparing a Neisseria antigen suitable for vaccine preparation comprising the steps of culturing a strain of Neisseria and recovering a cell surface antigen therefrom, the improvement which comprises culturing a strain of Neisseria substantially incapable of producing a PIII-like protein. In yet another embodiment the invention relates to an improvement in a method for the immunization of a mammal against Neisseria infection by employing a vaccine comprising an antigen derived from the cell surface of Neisseria; the improvement which comprises utilizing as a source of the antigen a strain of Neisseria substantially incapable of producing a PIII-like protein. In a final embodiment the invention provides a proteosome preparation in which the protein is derived from a strain of Neisseria incapable of producing immunologically functional PIII-like protein.

BRIEF DESCRIPTION OF THE DRAWINGS

FIG. 1 illustrates diagrammatically the steps in the formation of plasmid Construct I.

FIG. 2 illustrates diagrammatically the steps in the formation of plasmid Construct II.

DETAILED DESCRIPTION OF INVENTION

This invention relates to a novel class of Neisseria mutants characterized by the fact that the mutants are unable to produce immunologically functional PIII-like molecules. This class of mutants is particularly useful as sources of antigenic material for use in Neisseria vaccines.

As used herein the following terms have the following meanings:

Nucleotide—A monomeric unit of DNA or RNA consisting of a sugar moiety (pentose), a phosphate, and a nitrogenous heterocyclic base. The base is linked to the sugar moeity via the glycosidic carbon (1' carbon of the pentose) and the combination of base and sugar is called a nucleoside. The base characterizes the nucleoside. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the DNA nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the DNA sequence GCTGGTTGTAAG theoretically may be expressed in three reading frames or phases, each of which affords a different amino acid sequence:

GCT GGT TGT AAG-Ala-Gly-Cys-Lys

G CTG GTT GTA AG-Leu-Val-Val

GC TGG TTG TAA G-Trp-Leu-(STOP)

However, only one of the above reading frames encodes the correct genetic information. The translational start signal is recognized by the ribosome and accessory initiation factors to fix the correct reading frame.

Polypeptide—A linear array of amino acids connected one to the other by peptide bonds between the α-amino and carboxy groups of adjacent amino acids.

Genome—The entire DNA of a cell or a virus. It includes inter alia the structural genes coding for individual polypeptides as well as regulatory sequences such as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide. Structural genes may also have RNAs as their primary product such as transfer RNAs (tRNAs) or ribosomal RNAs (rRNAs).

Transcription—The process of producing RNA from a structural gene.

Translation—The process of producing a polypeptide from mRNA.

Expression—The process undergone by a structural gene to produce a product. In the case of a protein product it is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism maybe changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cloning Vehicle—A plasmid, phage DNA or other DNA sequence which is able to replicate in a host cell, characterized by one or a small number of endonuclease recognition sites at which such DNA sequences maybe cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction or DNA replication.

Recombinant DNA Molecule—A molecule consisting of segments of DNA from different genomes which have been joined end-to-end and have the capacity to infect some host cell and be maintained therein.

Expression Control Sequence—A sequence of nucleotides that controls and regulates expressing of structural genes when operatively linked to those genes. They include the lac system, major operator and promoter regions of phage λ, the control region of fd coat protein and other sequences known to control the expression of genes of prokaryotic or eukaryotic cells and their viruses.

Mutation—A hereditable change in the genetic information of an organism.

Mutant—An organism harboring a mutation. Generally expressing a discernible phenotype when compared to a standard reference strain of the species to which the organism belongs or to a wild-type population of that organism.

PIII-like proteins—Any protein occurring on the cell surface of Neisseria having the ability, like P-III of *N.* gonorrhoeae, to elicit and/or immunologically react with blocking antibodies, e.g. class 4 of *N. meninqitidis*.

Immunologically functional or antigenically significant—An amount of protein (i) capable of eliciting blocking antibody formation in an immunized mammal and/or (ii) capable of immunologically reacting with a blocking antibody.

Blocking Antibody—An antibody which by binding to an antigen blocks the attachment of other antibodies or cells with antigen receptors or otherwise inhibits the function of the other antibodies or cells.

In order to simplify the description of the invention, the following discussion will employ, as an example, the PIII protein of *N. gonorrhoeae*, however, the description is equally applicable to any PIII-like protein such as class 4 of *N. meningitidis*.

This invention solves the aforementioned difficulties in separating PIII from antigen preparations derived from cell membrane material, by providing a mutant strain genetically incapable of producing immunologically functional PIII. Depending upon the actual mutant generated a small amount of PIII or fragment thereof may be produced. Such levels of production are tolerable so long as the amount of PIII is not immunologically functional, i.e. antigenically significant. Such strains are considered to be substantially incapable of producing PIII. Further it is appreciated that the entire PIII protein may not be required for antigenicity, that is, antigenically functional fragments of PIII can exist and are variously referred to as antigenic determinant sites or epitopes. Thus, in the context of the present invention so long as the epitopes which elicit and/or react with the blocking antibodies are removed or rendered nonfunctional the remaining portions of the PIII gene may be expressed without particular consequence.

A number of different types of mutations can give rise to a mutant strain substantially incapable of producing antigenically significant PIII and are contemplated by this invention.

Point mutations characterized by the substitution of a single nucleotide in DNA (so called transition or transversion mutations) can cause the genetic "sense" of a codon to be changed thereby causing a different amino acid to be inserted into the protein chain (a so-called missense mutation). If the substituted amino acid is at a critical site necessary for blocking antibody binding, a PIII protein incapable of immunological functioning will result. Alternatively the nucleotide change could convert one of the 61 "sense" codons to one of the three terminator codons (a so-called nonsense mutation). If the position of the nonsense mutation is "upstream" from a critical epitope region, then protein synthesis will be terminated prior to reaching that region resulting in a truncated protein product lacking the required epitope. It is also possible to generate point mutations involving the addition or deletion of single nucleotides (as opposed to the substitution of single nucleotides). These +1/−1 events change the reading frame of the genetic message, rendering any information "down-stream" of the frameshift the equivalent of genetic garbage. As was the case with the nonsense mutations discussed above, if the frameshift mutations occurs "upstream" from a critical epitope, then the translation product will not contain the correct amino acid sequence because that region will be read out-of-frame. Although point mutation can clearly give rise to mutants with the required properties, i.e. the inability to produce antigenically significant PIII, because of the possibility of the re-substitution of the correct nucleotide (reversion) or the intergenic or extrageneic suppression of the mutation, point mutation is not the most preferred mechanism for generating the mutants of this invention.

Alternatively, it is possible to delete the entire PIII gene or at least significant portion thereof. It is also possible to interrupt the coding sequence of the PIII gene by inserting within the sequence, a piece of exogenous DNA. Further, it is possible to use a combination of both techniques, e.g., deleting a portion of the PIII gene and substituting therefor a piece of exogenous DNA.

Regardless of the method used to generate the desired PIII mutant if the mutation results in a recognizable phenotypic change then the desired "PIII-less" strains can be easily recovered. If however, a unique phenotype is not associated with the absence of immunologically functional PIII, then more elaborate procedures may be necessary. For example, since antibodies to PIII are available, one may screen for "PIII-less" strains by a filtration enrichment protocol.

In this case, because the function of PIII was not known, one could not a priori predict the phenotype of the "PIII-less" strains. Furthermore, because PIII was known to be a major cell membrane component, it was likely that mutants lacking PIII would not be able to synthesize a functional cell membrane and thus resulting in a lethal event for the cell. It was, therefore, surprising that "PIII-less" strains could be recovered at all.

As exemplified hereinbelow an exogenous marker gene can be introduced to indicate the absence of the PIII gene. Any method of inducing and recovering PIII mutants is acceptable so long as the strains recovered fail to produce antigenically significant amounts of PIII.

The invention may be more fully appreciated by reference to a particular example relating to the generation and recovery of a PIII mutant by insertion of a marker gene. The steps may be outlined as follows: providing a cloned PIII gene, providing a marker gene, introducing the marker gene into the PIII gene, transforming *N. gonorrhoeae* to yield a strain incapable of producing immunologically functional PIII.

With reference to FIGS. 1 and 2 the following represents a detailed outline of the procedures for generating a mutant strain of Neisseria substantially incapable of producing immunologically functional PIII.

Cloning Of The Gene For P-III

Methods for cloning the gene for PIII have been described by Gotschlich et al. (*J. Exp. Med.* 164: 868–881 (1986), the entire contents of which are incorporated herein by reference.

Briefly, *E. coli* strain Y1089 lysogenized with λ gt 11 was grown in 500 ml NZCYM medium to an OD of 0.800 at 500 nm in a 2.8 liter Fernbach flask. The culture was heated to 44° C. over an open flame, and incubated for an additional 2 h at 37° C., and the organisms were harvested by centrifugation. The cells were suspended in 10 ml of λ dilution buffer (SM solution), 500 μl of chloroform and 100 μg of deoxyribonuclease were added, and the suspension was incubated for 20 min. The debris was removed by centrifugation at 2,500 g, and the pellet was resuspended in 5 ml of SM solution and recentrifuged. This washing step was repeated and the phage isolated from the pooled supernates were purified by sedimintation followed by flotation in solutions of CsCl.

Genomic DNA was prepared from gonococcal strain R10. 500 μg of DNA was treated with Eco R1 methylase. The DNA was sheared by sonication and then treated with mung bean nuclease to produce blunt ends. Approximately 30 μg of this DNA was fractionated by agarose gel electrophoresis, and the fraction corresponding to 600–2,300 bp was electroeluted. The material was ligated to Eco R1 linkers that had been phosphorylated using polynucleotide kinase. After ligation, the DNA was subjected to extensive Eco R1 digestion, and small nucleotides were separated from the DNA by spermine precipitation, followed by chromatography over a 1 ml column of Sephacryl 200.

50 ng of insert and 2 µg of vector were ligated with T4 ligase and added to a λ packaging mix and titered. The bank was amplified on three large petri dishes, and was estimated to be derived from $4.6 \times 10^5$ plaques, of which 54% contained inserts as judged by lack of β-galactosidase activity.

Gonococcal PI was purified as from strain 120176-2, and used to immunize a rabbit. The resultant serum was passed over an affinity column consisting of purified PI covalently linked to CNBr-activated Sepharose and eluated with 100 mM glycine HCl buffer, pH 2.3, containing 0.1% Triton X-100. Immunological screening was performed by allowing ~$10^5$ plaques to grow for 2.5 h at 42° C., overlaying with a dry nitrocellulose filter previously impregnated with 10 mM IPTG, incubating for 2 h at 37° C., and washing the filter in blocking buffer (10 mM Tris HCl, pH 7.5, containing 0.5 M NaCl and 0.5% Tween 20) three times for 10 min. The filters were incubated overnight with antiserum diluted in the blocking buffer, washed three times, incubated with alkaline phosphatase-conjugated antiimmunoglobulin for 2 h, washed three times with blocking buffer, washed once with 50 mM Trizma base with 3 mM $MgCl_2$, and then incubated with alkaline phosphatase substrate dissolved in the Trizma base buffer and incubated at 37° C.

The phage from plaques identified by immunological activity were purified and used to infect strain Y1089 to produce lysogens. These were induced for phage production by shifting incubation temperature to 44° C., and then induced with IPTG for antigen production. SDS-PAGE was performed on cells lysed in the SDS-containing loading buffer. Electrophoretic transfer to nitrocellulose or to Durapore membranes was performed and the Western blots were probed immunologically as described above, or using radioactive protein A (Amersham Corp., Arlington Heights, Ill.). Antibodies were affinity purified from rabbit serum using the products of plaques fixed to nitrocellulose. Dense lawns of plaques (~50,000) were grown on E. coli Y1090 at 42° C. for 2.5 h, overlaid with an IPTG-containing nitrocellulose filter, and incubated for 2 h at 37° C. The filter was washed with blocking buffer as described above, allowed to react with 50 µl of serum diluted to 5 ml with blocking buffer for 4 h, washed three times with blocking buffer, and once with 150 mM NaCl. The antibodies were eluted with 5 ml of 150 mM glycine HCl, pH 2.3, for 15 min. The eluate was promptly neutralized and used for Western blots.

DNA hybridization analyses were performed according, to the method of Meinkoth and Wahl (*Anal. Biochem.* 138: 267–284 (1984) and stringent washing conditions were used (1×SSC at 69° C.).

A clone isolated by the above procedure (clone 33) has been shown to contain the gene for PIII and its DNA sequence has been determined. Gotschlich et al. (J. Exp. Med. 165: 471–492 (1987)), the entire contents of which are incorporated herein by reference. A sample of this clone as a lysogen in *E. coli* was deposited with the American Type Culture Collection, 10801 University Blvd., Manassas, Va. 20110-2209 USA on Jun. 28, 1988 and was designated ATCC No. 53786.

Construction Of A PIII Gene Containing A Marker Gene Insert

The general approach employed was to clone a marker gene into a unique Xba I site at nucleotide 601 in the PIII gene. All recombinant DNA manipulations were done except where otherwise specifically indicated, according to the protocols described by Maniatis et al. ("Molecular Cloning: a laboratory manual", Cold Spring Harbor Laboratory, Cold Spring Harbor, N.Y. (1982)).

Of course any marker gene is suitable so long as it confers upon the cell harboring such a gene a recognizable phenotype, including but not necessarily limited to antibiotic resistance or sensitivity, color or morphological change, enzyme activity, auxotrophy or relief from such a condition.

Construct I

This construction illustrates the insertion of a β-lactamase marker into the unique XbaI site. The λgt11 clone 33 was treated with EcoRI to excise the insert. This insert was ligated into EcoRI cut plasmid vector pMOB45 (ATCC No. 37106) and clones resistant to tetracycline, but sensitive to chloramphenicol were selected and plasmid was prepared. PMOB45 was chosen as a vector because it does not contain a β-lactamase gene and lacks any XbaI sites. Clones are characterized by preparation of plasmids and characterization with EcoRI digestion. A particular isolate designated pMOB45/33-2 was used for further constructions.

The β-lactamase gene was prepared in the following manner. The gonococcal plasmid pFA3 (Mayer, L. et al., *J. Bacteriol.* 154: 1498 (1983)) was purified by the alkaline lysis method described by Ish-Horowicz (*Nucl. Acid Res.* 9:2989 (1981)). The β-lactamase is contained on a 2.2 kb BamHI fragment which was isolated by restriction enzyme digestion, agarose gel electrophoresis and electroelution of the restriction enzyme fragment.

The cloning of the β-lactamase gene into the PIII gene was performed as follows. Approximately 2.5 µg of pMOB45/33-2 was digested with XbaI and after digestion the enzyme was inactivated by heating to 70° C. for 10 min. Approximately 1 µg of purified β-lactamase gene was added, and then using the Klenow fragment of DNA polymerase the 5' overhanging ends left by the restriction enzyme digestions were filled in order to obtain blunt ends. The fragments were ligated with T4 DNA ligase and transformed into competent cells of E. coli strain HB101 (ATCC No. 33694) and placed on selective medium containing tetracycline and carbenicillin. Twelve colonies were selected and plasmids were isolated from four of these and these were called respectively A–D. Restriction mapping with EcoRI digestion indicated that plasmids A, C and D gave rise to the expected fragments. In order to determine the orientation of the β-lactamase gene in the construct restriction mapping with PstI and PvuI were performed. These studies indicated that plasmid A and C gave rise to the same restriction fragments while plasmid D gave rise to a different pattern indicating that the β-lactamase gene had been cloned in both orientations. Plasmids C and D were prepared in larger quantities (Ish-Horowicz, supra) and then further purified by CsCl equilibrium density gradient centrifugation. Aliquots of approximately 5 µg were methylated using HaeIII methylase using the protocol recommended by the vendor (New England Biolabs Inc.) This step was performed in order to protect the DNA from one of the restriction enzymes possessed by the gonococcus which is an isoschizomer of HaeIII (Torres A. et al., *J. Clin. Micro* 20: 687–690 (1984). Finally the plasmid was digested with EcoRI to release the modified gonococcal DNA fragment and the DNA used to transform competent gonococci of strain F62.

Transformation was carried out by incubating approximately $5 \times 10^7$ competent gonococci in gonococcal broth supplemented with 1 mM $MgCl_2$ with 2 pg of plasmid C or D prepared as described above, for a period of 60 min in a volume of 1 ml. Three ml of fresh medium was added and the culture allowed to grow for an additional 6 h. Various dilutions of the culture were then plated on GC agar (Swanson, J., Infect. Immun. 10: 320 (1978)) which contained a concentration gradient of ampicillin. The gradient was established by adding 50 μl of a 1 mg/ml solution of ampicillin to the center of the plate and after a few minutes spreading this drop in a circular motion over the plate with a sterile glass rod. Over the next 48 h colonies which grew well at the edge of the zone of inhibition caused by the antibiotic gradient were selected and propagated on GC medium containing 3 μg/ml of ampicillin. These isolates were tested for the production of β-lactamase by the nitrocellolose disk method. A single β-lactamase producing colony was isolated from the transformation mix to which plasmid D had been added, and the gonococcal strain was designated 2D.

Strain 2D is a piliated gonococcal strain which grows normally and produces no PIII perceptible by SDS-PAGE following Coomassie blue staining (Laemmli, U., Nature 227: 680 (1970)). The absence of the PIII protein was further confirmed by Western blotting (Towbin. H. et al., Proc. Nat'l. Acad. Sci. USA 72: 4350–54 (1979)) using both rabbit antiserum specific for PIII and a monoclonal antibody to PIII. DNA isolated from strain 2D was examined by DNA hybridization using either a DNA probe specific for the PIII gene or for the β-lactamase gene. It was demonstrated that restriction fragments containing the PIII gene were 2.2 kb larger representing the addition of the β-lactamase gene and that restriction fragments of identical size were detected with the β-lactamase probe in DNA extracted from strain 2D, but not from the parent strain F62. Furthermore, DNA from strain 2D was used to transform several other gonococcal strains such as UUI (Lynch E.C. et al., Biophys J. 45: 104–107 (1984)) and PGH 3–2 (Brinton, C. C. et al., "Immunobiology of N. gonorrhoeae" pg 155–178 Amer. Soc. for Micro. (1978)) and in each instance mutants lacking the ability to produce PIII were generated.

Construct II

Following generally the procedures outlined for Construct I, a second construct was generated employing a marker gene conferring resistance to erythromycin instead of the β-lactamase gene. This gene called Erm was isolated from the Bacillus subtilis plasmid pIM13 by digestion with ClaI and HindIII (Projan S. J. et al., J. Bacteriol. 169: 5131–5139 (1987)) and cloned into a plasmid vector pHSS6 (Seifert, H.S. et al., Proc. Nat'l. Acad. Sci. USA, 83: 735–739 (1986)) cut with the same restriction enzymes. pHSS6/Erm was grown in broth, plasmid prepared and following digestion with ClaI and HindIII and blunting of 5' overhanging sequences with the Klenow fragment of DNA polymerase. The DNA was separated by electrophoresis on low melting point agarose and the band representing the Erm gene excised.

The EcoRI insert of λgt11 clone 33 was cloned into the vector pUC9 (Pharmacia). This plasmid, pUC9/33, was digested with XbaI and the 5' overhanging sequences filled using the Klenow fragment of DNA polymerase. The DNA was separated by electrophoresis on low melting point agarose, and the major DNA band was excised. This DNA was mixed with the purified filled Erm gene and ligated as described by Struhl (Biotechniques 3: 452–53 (1985)) and used to transform competent strain DH5 and placed on LB agar medium containing 50 μg/ml of carbenicillin an 100 μg/ml of erythromycin. A number of clones were isolated and characterized by restriction mapping with EcoRI.

A particular clone designated pUC9/PIII/Erm was digested with EcoRI and the insert ligated into EcoRI cut vector pHSS6 and transformants selected on LB plates containing 40 μg/ml kanamycin and 100 μg/ml of erythromycin, and a number of clones were isolated and characterized by restriction mapping with EcoRI and the PIII/Erm gene isolated by EcoRI digestion from clone #1 was used as described below.

The PIII/Erm gene was cloned into EcoRI digested plasmid pLES2, a shuttle vector capable of growing in gonococci (Stein, D.C. et al., Gene 25: 241–47 1983)). This was accomplished by ligation and transformation into competent E. coli and selection on LB agar containing carbenicillin and erythromycin. The plasmid was isolated and methylated with HaeIII methylase as described before. The DNA was digested with EcoRI in order to release the PIII/Erm fragment (the gonococcal DNA interrupted by the antibiotic marker) and the DNA used to transform competent F62 gonococci as described above. Following transformation and further growth in fluid medium for 6 h dilutions of the transformation mixture were plated on GC agar plates with a gradient of erythromycin established as described above using 50 μl of a 500 μg/ml solution of erythromycin.

At 48 h many colonies grew well in the zone of antibiotic inhibition and these were picked and propagated on GC agar containing 0.1 μg/ml of erythromycin. These clones grew well and by western blotting using a monoclonal antibody were shown to be devoid of detectable PIII.

The N. gonorrhoeae strain 2D incapable of expressing antigenically significant amounts of PIII was deposited with the American Type Culture Collection, 10801 University Blvd., Manassas, Va. 20110–2209 USA on Jun. 28, 1988 and was designated ATCC No. 53787.

Protein I Isolation

PI was isolated from the PIII minus Strain 2D using a variation of methods previously described (Blake M. S. et al., Infect. Immun., 36:277 (1982); Blake, M. S. et al., J. Exp. Med., 159:452 (1984); Lytton, E. J. et al., J. Exp. Med., 164:1749 (1986)). The mutant bacteria were harvested by centrifugation and slowly resuspended in an equal volume of 1.0 M sodium acetate, pH 4.0 containing 1 mM 2,3-dimercaptopropanol. To this suspension were added 6 volumes of 5% (w/v) Zwittergent N-tetradecyl-N,N-dimethyl-3-ammonia-propanesulfonate (Z 3,14)(Calbiochem-Behring Corp., La Jolla, Calif.) in 0.5 M $CaCl_2$ and stirred for 1 h. Two volumes of absolute ethanol were added slowly to bring the concentration to 20% (v/v). The precipitate, which contained most of the nucleic acids, was removed by centrifugation at 17,000×g for 15 min. The concentration of ethanol in the supernate was increased to 80% (v/v) and the resultant precipitate was recovered by centrifugation. This precipitate, which contained PI, was resuspended in 50 mM Tris-HCl, pH 8.0, 10 mM EDTA and 5% Z 3,14. This mixture was stirred for 1 h and clarified by centrifugation at 12,000×g for 15 min. The soluble material was applied to two columns (2.6×30 cm) linked in tandem, one packed with DEAE Sepharose CL-6B (Pharmacia Fine Chemicals, Piscataway, N.J.) and the second packed with CM Sepharose CL-6B (Pharmacia), both equilibrated with 50 mM Tris-HCl, pH 8.0 with 10 mM EDTA and 0.05% Z 3,14. The eluate was monitored by 280 nm absorbance and SDS-PAGE. After sample application, the columns were washed with equilibration buffer until the 280 nm absorbance reached baseline. The majority of PI flowed through both columns. The flow through was saved and the PI was precipitated by the addition of absolute ethanol to a concentration of 80% (v/v). The precipitate was retrieved by centrifugation at 12,000×g for 15 min. This precipitate was dissolved in 10 ml of 50 mM Tris-HCl, pH 8.0 with 10 mM EDTA and 5% Z 3,14 and applied to a column (2.6×170 cm) of Sephacryl S-300 (Pharmacia). The elution buffer was 100 mM Tris-HCl, 200 mM NaCl, 10 mM EDTA, 0.05% Z 3,14 at pH 8.0 and the flow rate was 10 ml/h. Fractions of 7.5 ml were monitored for absorbance at 280 nm, collected, and analyzed by SDS-PAGE. The fractions that contained PI were pooled and utilized in the immunizing preparation.

Vaccine Preparation

Preparation of vaccines which contain peptide sequences as active ingredients is well understood in the art. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some case, oral formulations. For suppositories, traditional binders and carriers my include, for example, polyalkalene glycols or triglycerides; such suppositories maybe formed from mixtures containing the active ingredient in the ran of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%–95% of active ingredient, preferably 25–70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

Alternatively, PI containing vaccines may be prepared in the form of liposomes. Liposomes were prepared by a variation of a described method *Mimms, L. T. et al., Biochemistry* 20:833 (1981) as follows: (1) The detergent in which the PI was dissolved was changed to D-octyl-glucoside (OG)(Aldrich Chemical Co., Milwaukee, Wis.) by precipitating the PI by the addition of ethanol, 50 mM sodium acetate to a concentration of 66.7% (v/v), centrifuging this mixture at 10,000×g for 10 min, and resuspending the precipitate in 10% (w/v) OG in 10 mM Hepes pH 7.2; (2) The liposomal lipids, synthetic phosphatidyl ethanolamine (PE) and phosphatidyl choline (PC)(Avanti Inc., Birmingham, Ala.) dissolved in chlorofrom (20 mg/ml), were mixed in a ratio of 4:1 (PE:PC) and dried in a thin layer on the inside of a acid cleaned test tube by rotary evaporation; (3) PI in a ratio of 50:1 (lipid:PI, w/w) in the OG was added to the dried PC/PE mixture which dissolved the lipids and gave a clear solution; (4) The solution was dialyzed extensively against PBS pH 7.2 to remove the OG and induce liposome formation; and (5) The dialyzed solution was sonicated (Branson Sonic Water Bath, Plainview, N.Y.) to form small unilammellar vesicles (SUV).

Finally, other investigators have found that purified Neisseria porins can be immunogenic when formed into pure protein vesicles—proteosomes ((Lowell, G. H. et al., *J. Exp. Med.* 167:658 (1988); Lowell, G. H. et al., *Science* 240:800 (1988)). Isolated PI from the PIII minus gonococci were also utilized to produce proteosomes to see if functional antibodies to PI and the living organism can be produced with minimal additives and adjuvants. Purified PI was ethanol precipatated as above (80% v/v) and then resuspended in 10% D-octyl-glucoside (Aldrich) in 10 nM Hepes pH 7.2. The mixtures were then dialyzed twice against 10 mM phosphate buffer, pH 8.0. An oily mixture was obtained and its protein concentration was calculted (Pierce).

This invention contemplates within its scope the use of the "PIII-less" mutants as sources of proteosome protein. Thus the proteosomes formed according to this invention do not have the disadvantage of PIII contamination and thus will not provoke an undesirable immunological response when used alone or as an adjuvant with other antigens.

The various liposome or proteosome vaccines are used to immunize rabbits and mice and the induced immune response is evaluated according to established procedures (Wetzler, L M. et al., Proc. 5th Int'l Path. Neisseria Conf. Sep. 1986, Netherlands; UCLA Symposia: Technol. Advances in Vaccine Devel., Lasky L.ed., 1988).

What is claimed is:

1. An isolated mutant strain of *Neisseria gonorrhoeae* or *Neisseria meningitidis* incapable of producing a PIII protein or class 4 protein that (i) elicits blocking antibodies against the PIII or class 4 protein that inhibit bactericidal activity or (ii) immunologically reacts with said antibodies.

2. An isolated mutant strain of *Neisseria gonorrhoeae* according to claim 1.

3. An isolated mutant strain of *Neisseria meningitidis* according to claim 1.

4. A biologically pure culture of a mutant strain of *Neisseria qonorrhoeae* or *Neisseria meningitidis* incapable of producing a PIII protein or class 4 protein that (i) elicits blocking antibodies against the PIII or class 4 protein that inhibit bactericidal activity or (ii) immunologically reacts with said antibodies.

5. The biologically pure culture according to claim 4, wherein the strain is *Neisseria gonorrhoeae* ATCC No. 53787.

6. *Neisseria gonorrhoeae* mutant strain ATCC No. 53787.

7. A composition comprising the total lysate of a biologically pure culture of a mutant strain of *Neisseria gonorrhoeae* or *Neisseria meningitidis* incapable of producing a PIII protein or class 4 protein that (i) elicits blocking antibodies against the PIII protein or the class 4 protein that inhibit bactericidal activity or (ii) immunologically reacts with said antibodies, wherein the composition is free of immunologically functional PIII protein and immunologically functional class 4 protein.

8. The composition of claim 7, wherein the mutant strain is *Neisseria gonorrhoeae* ATCC No. 53787.

9. A method for the immunization of a mammal against Neisseria infection, comprising the steps of:
  (a) isolating at least one antigen from a biologically pure culture of a mutant strain of *Neisseria gonorrhoeae* or *Neisseria meningitidis* incapable of producing a PIII protein or class 4 protein that (i) elicits blocking antibodies against the PIII or class 4 protein that inhibit bactericidal activity or (ii) immunologically reacts with said antibodies;
  (b) admixing the at least one antigen with a physiologically-acceptable excipient to form an antigenic composition; and
  (c) administering the antigenic composition to the mammal.

10. The method according to claim 9 wherein the mutant strain is *Neisseria gonorrhoeae* ATCC No. 53787.

11. A method of preparing an antigenic composition capable of eliciting the production of antibodies which recognize *Neisseria gonorrhoeae* or *Neisseria meningitidis*, the method comprising the steps of:
  1) culturing a biologically pure mutant strain of *Neisseria gonorrhoeae* or *Neisseria meningitidis* incapable of producing a PIII protein or a class 4 protein that (i) elicits blocking antibodies against the PIII or class 4 protein that inhibit bactericidal activity or (ii) immunologically reacts with said blocking antibodies;
  2) recovering at least one cell-surface antigen from the cultured strain; and
  3) admixing an amount of the at least one recovered antigen sufficient to induce a host administered with the composition to produce antibodies which recognize *Neisseria gonorrhoeae* or *Neisseria meningitidis* with a physiologically acceptable excipient.

12. The method according to claim 11 wherein the mutant strain is *Neisseria gonorrhoeae* ATCC No. 53787.

13. The method according to claim 12 wherein the at least one cell-surface antigen is selected from the group consisting of PI, PII, pilin, lipopolysaccharide and iron binding protein.

14. The method according to claim 12 wherein the cell-surface antigen is PI.

15. A method of producing antibodies in a host, which antibodies recognize *Neisseria gonorrhoeae* or *Neisseria meningitidis*, the method comprising the steps of:
  (a) isolating at least one antigen from a biologically pure culture of a mutant strain of *Neisseria gonorrhoeae* or *Neisseria meningitidis* incapable of producing a PIII protein or class 4 protein that (i) elicits blocking antibodies against the PIII protein or the class 4 protein that inhibit bactericidal activity or (ii) immunologically reacts with said blocking antibodies;
  (b) admixing the at least one antigen with a physiologically-acceptable excipient to form an admixture;
  (c) administering the admixture to the host.

16. The method according to claim 15, wherein the mutant strain is *Neisseria gonorrhoeae* ATCC No. 53787.

17. The method according to claim 15 or 16, wherein the at least one antigen consists essentially of at least one cell-surface antigen.

18. The method according to claim 15 or 16, wherein the at least one antigen consists essentially of an antigen selected from the group consisting of PI, PII, pilin, lipopolysaccharide, and iron binding protein.

19. The method according to claim 18, wherein the antigen is PI.

20. The method according to claim 18, wherein the excipient is a liposome.

21. The method according to claim 18, wherein the excipient is a proteosome.

22. The method according to claim 15 or 16, wherein the excipient is a liposome.

23. The method according to claim 15 or 16, wherein the excipient is a proteosome.

24. The method according to claim 15 or 16, wherein at least a fraction of the antibodies so-produced have bactericidal activity against *Neisseria gonorrhoeae* or *Neisseria meningitidis*.

* * * * *